(12) United States Patent
Bondy et al.

(10) Patent No.: US 7,956,184 B2
(45) Date of Patent: Jun. 7, 2011

(54) PYRIDAZINE COMPOUND AND USE THEREOF

(75) Inventors: Steven S. Bondy, Danville, CA (US); David A. Oare, Belmont, CA (US); Winston C. Tse, San Mateo, CA (US)

(73) Assignees: Gilead Sciences, Inc., Foster City, CA (US); K.U. Leuven Research & Development, Leuven (BE); Gerhard Puerstinger, Igls (AT)

( * ) Notice: Subject to any disclaimer, the term of this patent is extended or adjusted under 35 U.S.C. 154(b) by 0 days.

(21) Appl. No.: 12/708,119

(22) Filed: Feb. 18, 2010

(65) Prior Publication Data

US 2010/0152444 A1 Jun. 17, 2010

Related U.S. Application Data

(62) Division of application No. 11/825,598, filed on Jul. 6, 2007, now Pat. No. 7,754,720.

(60) Provisional application No. 60/819,289, filed on Jul. 7, 2006, provisional application No. 60/832,403, filed on Jul. 21, 2006, provisional application No. 60/832,769, filed on Jul. 24, 2006.

(51) Int. Cl.
C07D 403/06 (2006.01)

(52) U.S. Cl. ....................................... 544/238

(58) Field of Classification Search .................. 544/238
See application file for complete search history.

(56) References Cited

U.S. PATENT DOCUMENTS

| | | |
|---|---|---|
| 2,191,978 A | 2/1940 | Balle et al. |
| 2,411,662 A | 11/1946 | Martin et al. |
| 2,516,674 A | 7/1950 | Havertown et al. |
| 2,548,863 A | 4/1951 | Havertown et al. |
| 3,985,891 A | 10/1976 | Kutter et al. |
| 4,358,387 A | 11/1982 | Zoleski et al. |
| 4,565,816 A | 1/1986 | Neumann |
| 4,692,443 A | 9/1987 | Katner |
| 4,804,658 A | 2/1989 | Manley et al. |
| 4,914,108 A | 4/1990 | Khanna et al. |
| 4,988,707 A | 1/1991 | Stealey et al. |
| 4,990,518 A | 2/1991 | Khanna et al. |
| 5,011,832 A | 4/1991 | Dininno et al. |
| 5,019,581 A | 5/1991 | Khanna et al. |
| 5,057,517 A | 10/1991 | Johnston et al. |
| 5,137,896 A | 8/1992 | Van Daele |
| 5,208,242 A | 5/1993 | Khanna et al. |
| 5,227,384 A | 7/1993 | Khanna et al. |
| 5,302,601 A | 4/1994 | Khannal et al. |
| 5,332,744 A | 7/1994 | Chakravarty et al. |
| 5,374,638 A | 12/1994 | Dhanoa et al. |
| 5,405,964 A | 4/1995 | Mederski et al. |
| 5,438,063 A | 8/1995 | Osswald et al. |
| 5,446,032 A | 8/1995 | Whittaker et al. |
| 5,486,525 A | 1/1996 | Summers, Jr. et al. |
| 5,585,492 A | 12/1996 | Chandrakumar et al. |
| 5,587,372 A | 12/1996 | Aszodi et al. |
| 5,607,944 A | 3/1997 | Linz et al. |
| 5,719,306 A | 2/1998 | Chandrakumar et al. |
| 5,723,492 A | 3/1998 | Chandrakumar et al. |
| 5,854,265 A | 12/1998 | Anthony |
| 5,859,035 A | 1/1999 | Anthony et al. |
| 5,872,136 A | 2/1999 | Anthony et al. |
| 5,874,452 A | 2/1999 | Anthony |
| 5,880,140 A | 3/1999 | Anthony |
| 5,883,105 A | 3/1999 | Anthony |
| 5,939,557 A | 8/1999 | Anthony et al. |
| 6,051,574 A | 4/2000 | Anthony |
| 6,063,930 A | 5/2000 | Dinsmore et al. |
| 6,080,870 A | 6/2000 | Anthony et al. |
| 6,329,381 B1 | 12/2001 | Kurimoto et al. |
| 6,376,515 B2 | 4/2002 | Zhu et al. |
| 6,479,508 B1 | 11/2002 | Beaulieu et al. |
| 6,492,384 B1 | 12/2002 | Mederski et al. |
| 6,627,651 B1 | 9/2003 | Shiraishi et al. |
| 6,767,654 B2 | 7/2004 | Tamao et al. |
| 6,770,666 B2 | 8/2004 | Hashimoto et al. |
| 6,803,374 B2 | 10/2004 | Priestley et al. |

(Continued)

FOREIGN PATENT DOCUMENTS

| | | |
|---|---|---|
| AU | 643289 B2 | 11/1993 |
| CA | 2093290 A1 | 10/1993 |
| CA | 2158996 A1 | 10/1994 |
| CA | 2357771 A1 | 7/2000 |
| CA | 2423800 | 3/2003 |

(Continued)

OTHER PUBLICATIONS

Akamatsu et al. (2002) "New Efficient Route for Solid-Phase Synthesis of Benzimidazole Derivatives," *J. Comb. Chem.* 4:475-483.

Baba et al., "Synergistic Antiviral Effects of Antiherpes Compounds and Human Leukocyte Interferon on Varicella-Zoster Virus In Vitro," Antimicrobial Agents Chemother. 25:515-517, 1984.

Baginski et al. (2000) "Mechanism of Action of a Pestivirus Antiviral Compound," *PNAS* 97(14):7981-7986.

Barlin and Fenn, "A Carbon-13 Nuclear Magnetic Resonance Study of Protonation in Imidazo[4,5-c]pyridines," Aust. J. Chem. 34:1341-1344 (1981).

(Continued)

*Primary Examiner* — James O Wilson
*Assistant Examiner* — Cecilia M Jaisle
(74) *Attorney, Agent, or Firm* — Barry F. McGurl

(57) ABSTRACT

A compound of formula (1) and its salts and solvates are provided for the treatment or prophylaxis of hepatitis C virus infections (1)

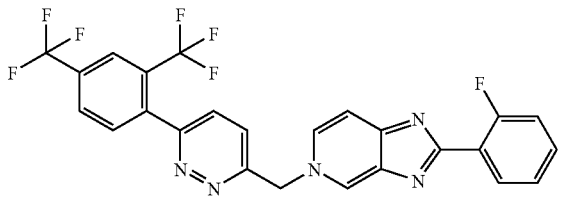

Methods of making and formulating compound (1) are provided.

1 Claim, 4 Drawing Sheets

U.S. PATENT DOCUMENTS

| | | | |
|---|---|---|---|
| 6,835,739 B2 | 12/2004 | Zhu et al. | |
| 6,844,367 B1 | 1/2005 | Zhu et al. | |
| 7,026,051 B2 | 4/2006 | Schauer et al. | |
| 7,098,231 B2 | 8/2006 | Poupart et al. | |
| 7,112,600 B1 | 9/2006 | Hashimoto et al. | |
| 7,223,785 B2 | 5/2007 | Beaulieu et al. | |
| 7,285,551 B2 | 10/2007 | Hashimoto et al. | |
| 7,294,457 B2 | 11/2007 | Kukolj et al. | |
| 7,754,720 B2 | 7/2010 | Bondy et al. | |
| 2003/0073836 A1 | 4/2003 | Priepke et al. | |
| 2003/0108862 A1 | 6/2003 | Kukolj et al. | |
| 2004/0082635 A1 | 4/2004 | Hashimoto et al. | |
| 2004/0097438 A1 | 5/2004 | Hashimoto et al. | |
| 2004/0097574 A1 | 5/2004 | Marshall | |
| 2004/0171626 A1 | 9/2004 | Beaulieu et al. | |
| 2004/0186125 A1 | 9/2004 | Poupart et al. | |
| 2005/0026921 A1 | 2/2005 | Eckhardt et al. | |
| 2005/0096337 A1 | 5/2005 | Ackermann et al. | |
| 2005/0222198 A1 | 10/2005 | Bondy et al. | |
| 2005/0239821 A1 | 10/2005 | Neyts et al. | |
| 2006/0052602 A1 | 3/2006 | Kim et al. | |
| 2006/0229336 A1 | 10/2006 | Kazmierski et al. | |
| 2006/0252791 A1 | 11/2006 | Bondy et al. | |
| 2007/0021472 A1 | 1/2007 | Zhu et al. | |
| 2007/0032497 A1 | 2/2007 | Hashimoto et al. | |
| 2007/0244148 A1 | 10/2007 | Bondy et al. | |
| 2008/0188516 A1 | 8/2008 | Bondy et al. | |
| 2008/0199427 A1 | 8/2008 | Bondy et al. | |
| 2009/0036460 A1 | 2/2009 | Dowdy et al. | |

FOREIGN PATENT DOCUMENTS

| | | | |
|---|---|---|---|
| CA | 2471566 A1 | 7/2003 | |
| CA | 2496249 A1 | 3/2004 | |
| DE | 4211474 | 10/1993 | |
| DE | 4211474 A1 | 10/1993 | |
| DE | 4230464 A1 | 3/1994 | |
| DE | 4236026 | 4/1994 | |
| DE | 4236026 A1 | 4/1994 | |
| DE | 4309969 | 9/1994 | |
| DE | 4309969 A1 | 9/1994 | |
| DE | 4318813 | 12/1994 | |
| DE | 4318813 A1 | 12/1994 | |
| EP | 0076530 A2 | 4/1983 | |
| EP | 0138552 | 4/1985 | |
| EP | 0138552 A2 | 4/1985 | |
| EP | 0228845 | 7/1987 | |
| EP | 0228845 A2 | 7/1987 | |
| EP | 0232937 A2 | 8/1987 | |
| EP | 0300726 A1 | 1/1989 | |
| EP | 0344414 A1 | 12/1989 | |
| EP | 0417745 A2 | 3/1991 | |
| EP | 0462009 A1 | 12/1991 | |
| EP | 0510260 A2 | 10/1992 | |
| EP | 0605836 A1 | 7/1994 | |
| EP | 0706795 | 4/1996 | |
| EP | 0706795 A2 | 4/1996 | |
| EP | 1132381 | 9/2001 | |
| EP | 1132381 A1 | 9/2001 | |
| EP | 1162196 | 12/2001 | |
| EP | 1386923 A1 | 2/2004 | |
| EP | 1400241 A1 | 3/2004 | |
| GB | 2158440 | 11/1985 | |
| GB | 2158440 A | 11/1985 | |
| GB | 2264115 A | 8/1993 | |
| HU | 78019 A2 | 5/1999 | |
| IL | 89588 | 3/1989 | |
| SU | 813921 A1 | 12/1986 | |
| SU | 1048742 A1 | 12/1986 | |
| SU | 851940 A1 | 4/1988 | |
| SU | 860463 A1 | 5/1998 | |
| WO | WO-9222556 A1 | 12/1992 | |
| WO | WO-93/02080 | 2/1993 | |
| WO | WO-9302080 A1 | 2/1993 | |
| WO | WO-93/14072 | 7/1993 | |
| WO | WO-9314072 A1 | 7/1993 | |
| WO | WO-9316075 A1 | 8/1993 | |
| WO | WO-9412461 A1 | 6/1994 | |
| WO | WO-9429321 A1 | 12/1994 | |
| WO | WO-9502597 A1 | 1/1995 | |
| WO | WO-9516687 A1 | 6/1995 | |
| WO | WO-96/11192 | 4/1996 | |
| WO | WO-9611192 A1 | 4/1996 | |
| WO | WO-96/12703 | 5/1996 | |
| WO | WO-9612703 A1 | 5/1996 | |
| WO | WO-9615111 A1 | 5/1996 | |
| WO | WO-99/27929 | 6/1999 | |
| WO | WO-9927929 A1 | 6/1999 | |
| WO | WO-00/20416 | 4/2000 | |
| WO | WO-00/20445 | 4/2000 | |
| WO | WO-0020400 A1 | 4/2000 | |
| WO | WO-0020416 A1 | 4/2000 | |
| WO | WO-0020425 A1 | 4/2000 | |
| WO | WO-0020445 A2 | 4/2000 | |
| WO | WO-00/39127 | 7/2000 | |
| WO | WO-00/40583 | 7/2000 | |
| WO | WO-0039127 A1 | 7/2000 | |
| WO | WO-0040583 A2 | 7/2000 | |
| WO | WO-0040586 A1 | 7/2000 | |
| WO | WO-0073307 A2 | 12/2000 | |
| WO | WO-0160315 A2 | 8/2001 | |
| WO | WO-0166526 A1 | 9/2001 | |
| WO | WO-0185172 A1 | 11/2001 | |
| WO | WO-0195910 A1 | 12/2001 | |
| WO | WO-0204425 A2 | 1/2002 | |
| WO | WO-02057425 A2 | 7/2002 | |
| WO | WO-02067942 A2 | 9/2002 | |
| WO | WO-03/004020 | 1/2003 | |
| WO | WO-03/007945 | 1/2003 | |
| WO | WO-03000254 A1 | 1/2003 | |
| WO | WO-03/004020 A1 | 1/2003 | |
| WO | WO-03/007945 A1 | 1/2003 | |
| WO | WO-03/010140 | 2/2003 | |
| WO | WO-03/010141 | 2/2003 | |
| WO | WO-03/010140 A2 | 2/2003 | |
| WO | WO-03/010141 A2 | 2/2003 | |
| WO | WO-03/014229 A1 | 2/2003 | |
| WO | WO-03/026587 A2 | 4/2003 | |
| WO | WO-03/057205 | 7/2003 | |
| WO | WO-03/057205 A2 | 7/2003 | |
| WO | WO-2004/005286 | 1/2004 | |
| WO | WO-2004005286 A2 | 1/2004 | |
| WO | WO-2004018468 A2 | 3/2004 | |
| WO | WO-2004019935 A1 | 3/2004 | |
| WO | WO-2004033455 A2 | 4/2004 | |
| WO | WO-2004043913 A2 | 5/2004 | |
| WO | WO-2004054974 A2 | 7/2004 | |
| WO | WO-2004/072243 | 8/2004 | |
| WO | WO-2004067516 A1 | 8/2004 | |
| WO | WO-2004072243 A2 | 8/2004 | |
| WO | WO-2005/063744 | 7/2005 | |
| WO | WO-2005063744 A2 | 7/2005 | |
| WO | WO-2006/033703 | 3/2006 | |
| WO | WO-2006029966 A1 | 3/2006 | |
| WO | WO-2006033703 A1 | 3/2006 | |
| WO | WO-2006069193 A2 | 6/2006 | |
| WO | WO-2007063744 A1 | 6/2007 | |
| WO | WO-2008005519 A2 | 1/2008 | |
| WO | WO-2009009001 A1 | 1/2009 | |

OTHER PUBLICATIONS

Barlin and Fenn, "The Preparation and 1H NMR Spectra of Some N-Methylpurines and Related Compounds," Aust. J. Chem. 36:633-638 (1983).

Barlin, "Ionisation Constants of Heterocyclic Substances, Part VIII. 1,3,5-Triazindenes," J. Chem. Soc. B: Phys. Org. 4:285-291, 1966.

Barraclough et al., "An Adventitious Synthesis of a 5-Methylimidazo[4,5-c]pyridine Derivative," Tet. Lett. 27:5997-6000 (1986).

Barraclough et al., "Inotropic"A"Ring Substituted Sulmazole and Isomazole Analogues," J. Med. Chem. 33:2231-2239 (1990).

Brown et al., "Purine Analogues as Amplifiers of Phleomycin. V. Thioethers of Several Heterocyclic Systems with One or Two Rings," Aust. J. Chem. 32:2713-2726 (1979).

Chou et al., "Quantitative Analysis of Dose-Effect Relationships: The Combined Effects of Multiple Drugs or Enzyme Inhibitors," Adv. Enzyme Reg. 22:27-55, 1984.
Cleve et al. (1971) "Derivate des Imidazo[4.5-b]- and Imidazo[4.5-c]pyridins," *Justus Liebigs Annalen Der Chemica* 747:158-171.
Curtin et al., "Discovery and Evaluation of a Series of 3-Acylindole Imidazopyridine Platelet-Activating Factor Anatagonists," J. Med. Chem. 41:74-95 (1998).
Elion et al., "Antagonists of Nucleic Acid Derivatives. VIII. Synergism in Combinations of Biochemically Related Antimetabolites," J. Biol. Chem. 208:477-488, 1954.
Final Rejection, Dec. 16, 2008, U.S. Appl. No. 11/019,830.
Final Rejection, Mar. 19, 2007, U.S. Appl. No. 11/316,050.
Fletcher et al., "Heterocyclic Systems," Nomenclature of Organic Adv. Ser. pp. 49-64, 1974.
Grazul et al. Natural Product Letters (1994) 5(3):187-195.
Greenfield et al., "Increase in the Stability and Helical Content of Estrogen Receptor Alpha in the Presence of the Estrogen Response Element: Analysis by Circular Dichroism Spectroscopy," Biochemistry 40:6646-6652, 2001.
Griesser, Chapter 8, The Importance of Solvates (pp. 211-230), in the text, Polymorphism: In the Pharmaceutical Industry, Hilfiker, 2006.
Guillory (in Britain ed.) "Polymorphism etc." NY:marcel Dekker Inc. 1999, 1-2, 183-226.
International Preliminary Examination Report (PCT/BE03100117) (mailed Sep. 3, 2004).
International Preliminary Report on Patentability for PCT/US2004/043112 dated Apr. 25, 2006.
International Preliminary Report on Patentability for PCT/US2005/026606 dated Feb. 20, 2007.
International Preliminary Report on Patentability for PCT/US2005/046477 dated Mar. 16, 2007.
International Preliminary Report on Patentability for PCT/US2007/015553 dated Jan. 13, 2009.
International Search Report for PCT/BE2003/000117 dated Dec. 16, 2003.
International Search Report for PCT/US2004/043112 dated Jun. 27, 2005.
International Search Report for PCT/US2005/026606 dated Feb. 13, 2006.
International Search Report for PCT/US2005/046477 dated Jun. 2, 2006.
International Search Report for PCT/US20071015553 dated Mar. 6, 2008.
International Search Report for PCT/US2008/008259 dated Oct. 14, 2008.
Jacob III, P., "Resolution of (+/−) 5-Bromonomicotine. Sythesis of (R)- and (S)-Nornicotine of High Enantiomeric Purity," J. Org. Chem. 47:4165-4167, 1982.
Johnson, A.W. Invitation to Organic Chemistry 1999 Jones and Bartlett: Missisauga, Canada p. 24.
Jones, Maitland Organic Chemistry Norton: New York, 1997, p. 84-99.
Kariv et al., "Improvement of 'Hit-to-Lead' Optimization by Integration of In Vitro HTS Experimental Models for Early Determination of Pharmacokinetic Properties," Comb. Chem. High Throughput Screen. 5:459-472, 2002.
Kino et al. (1993) "Studies on Cerebral Protective Agents, IV. Synthesis of Novel 4-Arylpyridine and 4-Arylpyridazine Derivatives with Anti-Anoxic Activity," *Chem. Pharm. Bull.* 41(1):136-162.
Kiyama et al. (1995) "Synthesis and Evaluation of Novel Nonpeptide Angiotensin II Receptor Antagonists: Imidazo[4,5-c]pyridine Derivatives with an Aromatic Substituent," *Chem. Pharm. Bull.* 43(3):450-460.
Lindenbach et al. (2005) "Unraveling Hepatitis C Virus Replication from Genome to Function," *Nature* 436:933-938.

Lochmuller et al., "Chromatographic Resolution of Enantiomers Selective Review," J. Chromatography 113:283-302, 1975.
Mederski et al. (1992) "Synthesis and Structural Assignment of Some N-Substituted imidazopyridine Derivatives," *Tetrahedron* 48(48):10549-10558.
Montgomery et al., "1-B-D-Arabinofuranosyl, etc.," J. Med. Chem., 1982,25,96-98.
Non-Final Rejection, Dec. 12, 2008, U.S. Appl. No. 10/519,756.
Non-Final Rejection, Mar. 12, 2008, U.S. Appl. No. 11/019,830.
Non-Final Rejection, Mar. 25, 2009, U.S. Appl. No. 12/022,557.
Non-Final Rejection, Oct. 29, 2008, U.S. Appl. No. 11/825,598.
Non-Final Rejection, Sep. 27, 2006, U.S. Appl. No. 11/316,050.
Okamoto et al., "Optical Resolution of Dihydropyridine Enantiomers by High-Performance Liquid Chromatography Using PhenylCarbamates of Polysaccharides as a Chiral Stationary Phase," J. Chromatography 513:375-378, 1990.
Paeshuyse et al., "A Novel, Highly Selective, etc.," J of Virology, Jan. 2006, 80(1), 149-160.
Penning et al., "Synthesis of Imidazopyridines as Potent Inhibitors of Leukotriene A4 Hydrolase," Bioorg. Med. Chem. Lett. 13:1137-1139, 2003.
Puerstinger et al. "Substituted 5-benzyl-2-phenyl-5H-imidazo[4,5-c]pyridines: A new class of pestivirus inhibitors" Bioorganic & Medicinal Chemistry Letters 2006, 16:5345-5349.
Puertstinger et al. "Antiviral 2,5-disubstituted imidazo[4,5-c]pyridines: From anti-pestivirus to anti-hepatitis C virus activity" Bioorganic & Medicinal Chemistry Letters 2007, 17:391-393.
Rigaudy et al., "Fundamental Heterocyclic Systems," Nomenclature of Organic Adv. Ser. pp. 53-76, 1979.
Robertson et al., "Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine," J. Med. Chem. 28:717-727 (1985).
Savarino et al., "Spectral Behaviour of Linked Heterocyclic Systems and Related Dyes," Spectrochim. Acta A: Mol. Biomol. Spectrosc. 49A:1379-1393 (1993).
Self et al. (1991) "Romazarit: A Potential Disease-Modifying Antirheumatic Drug," *J. Med, Chem.* 34:772-777.
Siddiqui et al., "3-Deaza- and, etc.," J. Med. Chem., 1995, 38, 1035-1038.
Stanovnik et al., "Methylation of Heterocyclic Compounds Containing NH, SH, and/or OH Groups by Means of N,N-Dimethylformamide Dimethyl Acetal," Aust. J. Chem. 34:1729-1738 (1981).
U.S. Appl. No. 11/658,625, filed Jul. 26, 2005, Kim et al.
U.S. Appl. No. 12/303,207, filed Feb. 12, 2008, Steven S. Bondy.
Vassilev et al., "Authentic and Chimeric Full-Length Genomic cDNA Clones of Bovine Viral Diarrhea Virus That Yield Infectious Transcripts," J. Viral. 71:471-478 (1997).
Vippagunta et al. "Crystalline Solid" Advanced Drug Delivery Reviews 48:3-26 (2001).
Wang et al., "Non-Nucleoside Analogue Inhibitors Bind to an Allosteric Site on HCV NS5B Polymerase. Crystal Structures and Mechanism of Inhibition," J. Biol. Chem. 278:9489-9495 (2003).
World Health Organization, Hepatitis C, Surveillance and Control, http://www.who.int/csr/disease/hepatitis/whocdscsrlyo2003/en/index4.html, downloaded Sep. 30, 2009.
Written Opinion for PCT/US2004/043112 dated Oct. 18, 2005.
Written Opinion for PCT/US2005/026606 dated Feb. 13, 2006.
Written Opinion for PCT/US2005/046477 dated Jun. 2, 2006.
Written Opinion for PCT/US2007/015553 dated Jan. 7, 2009.
Yutilov, et al. (1989) "Synthesis and Antiviral Activity of Spinaceamine Derivatives," *Khimiko-Farmatsevtichesku Zhumal* 23(1):56-59.
Zhang, "Inhibitors of Hepatitis C—A Review of the Recent Patent Literature," IDrugs 5: 154-158 (2002).
Zhang, S. (2001) "Studies on the Synthesis and Single Crystal Structure of 3-methyl-6-(p-methylphenyl) Pyridazine," *Sichuan Shifan Daxue Xuebao Ziran Kexueban* 24(4):384-387.

PYRIDAZINE COMPOUND AND USE THEREOF

BACKGROUND OF THE INVENTION

The hepatitis C virus is an enveloped, single-stranded, positive sense RNA virus in the family Flaviviridae. HCV mainly replicates within hepatocytes in the liver. Circulating HCV particles bind to receptors on the surfaces of hepatocytes and subsequently enter the cells. Once inside the hepatocyte, HCV utilizes the intracellular machinery necessary to accomplish its own replication. Lindenbach, B. Nature 436 (7053):932-8 (2005). The HCV genome is translated to produce a single protein of around 3011 amino acids. This "polyprotein" is then proteolytically processed by viral and cellular proteases to produce three structural (virion-associated) and seven nonstructural (NS) proteins.

HCV encodes two proteases, the NS2 cysteine autoprotease and the NS3-4A serine protease. The NS proteins then recruit the viral genome into an RNA replication complex, which is associated with rearranged cytoplasmic membranes. RNA replication takes places via the viral RNA-dependent RNA polymerase of NS5B, which produces a negative-strand RNA intermediate. The negative strand RNA then serves as a template for the production of new positive-strand viral genomes. Nascent genomes can then be translated, further replicated, or packaged within new virus particles. New virus particles presumably bud into the secretory pathway and are released at the cell surface.

HCV has a high rate of replication with approximately one trillion particles produced each day in an infected individual. Due to lack of proofreading by the HCV RNA polymerase, HCV also has an exceptionally high mutation rate, a factor that may help it elude the host's immune response.

Based on genetic differences between HCV isolates, the hepatitis C virus species is classified into six genotypes (1-6) with several subtypes within each genotype. Subtypes are further broken down into quasispecies based on their genetic diversity. The preponderance and distribution of HCV genotypes varies globally. For example, in North America genotype 1a predominates followed by 1b, 2a, 2b, and 3a. In Europe genotype 1b is predominant followed by 2a, 2b, 2c, and 3a. Genotypes 4 and 5 are found almost exclusively in Africa. Genotype is clinically important in determining potential response to interferon-based therapy and the required duration of such therapy. Genotypes 1 and 4 are less responsive to interferon-based treatment than are the other genotypes (2, 3, 5 and 6). Duration of standard interferon-based therapy for genotypes 1 and 4 is 48 weeks, whereas treatment for genotypes 2 and 3 is completed in 24 weeks.

The World Health Organization estimates that world-wide 170-200 million people (3% of the world's population) are chronically infected with HCV. Approximately 75% of these individuals are chronically infected with detectable HCV RNA in their plasma. These chronic carriers are at risk of developing cirrhosis and/or liver cancer. In studies with a 7-16 years follow-up, 7-16% of the patients developed cirrhosis, 0.7-1.3% developed hepatocellular carcinoma and 1.3-3.7% died of liver-related disease.

The only treatment option available today is the use of interferon α-2 (or its pegylated form) either alone or combined with ribavirin. However, sustained response is only observed in about 40% of the patients and treatment is associated with serious adverse effects. There is thus an urgent need for potent and selective inhibitors of HCV.

Relevant disclosures include U.S. Pat. Nos. 4,914,108; 4,988,707; 4,990,518; 5,137,896; 5,208,242; 5,227,384; 5,302,601; 5,374,638; 5,405,964; 5,438,063; 5,486,525; 6,479,508; and U.S. Patent Publication No. US2003/0108862 A1, Canadian Patent No. 2423800 A1, German Patent Nos. 4211474 A1, 4236026, 4309969, 4318813, European Patent Nos. EP 0 138 552 A2, EP 0 706 795 A2, EP 1 132 381 A1, Great Britain Patent No. 2158440 A, PCT Patent Publication Nos. WO 00/20416, WO 00/39127, WO 00/40583, WO 03/007945 A1, WO 03/010140 A2, WO 03/010141 A2, WO 93/02080, WO 93/14072, WO 96/11192, WO 96/12703, WO 99/27929, PCT-US2004/43112, PCT-BE2003/000117, PCT-US2005/26606, Akamatsu, et al., "New Efficient Route for Solid-Phase Synthesis of Benzimidazole Derivatives", 4:475-483, *J. COMB. CHEM.*, 2002, Baginski S G et al., Proc. Natl. Acad. Sci. U.S.A. 2000 Jul. 5; 97(14):7981-6). Cleve et al., "Derivate des Imidazo[4.5-b]- and lmidazo[4.5-c]pyridins", 747:158-171, *JUSTUS LIEBIGS ANNALEN DER CHEMICA*, 1971, Kiyama, et al., "Synthesis and Evaluation of Novel Nonpeptide Angiotensin II Receptor Antagonists: Imidazo[4,5-c]pyridine Derivatives with an Aromatic Substituent", 43(3):450-60, *CHEM PHARM BULL*, 1995, Mederski et al., "Synthesis and Structural Assignment of Some N-substituted Imidazopyridine Derivatives", 48(48): 10549-58, *TETRAHEDRON*, 1992, Yutilov et al., 23(1):56-9, *KHIMIKO-FARMATSEVTICHESKII ZHURNAL*, 1989. In addition, see WO 05/063744.

A need exists for compounds having desired anti-HCV therapeutic and/or prophylactic attributes, including high potency, selectivity and oral bioavailability (suitable for administration once or twice a day), low toxicity (including acceptable performance in the hERG patch clamp assay, absence of pulmonary permeability edema and no effect on QT interval), minimal or no metabolic activation/glutathione adduct formation, no evidence of genotoxicity, low metabolic turnover and low plasma clearance, wide-spectrum efficacy against HCV genotypes (especially 1a and 1b, 2 , 3 and 4), efficacy against HCV resistance mutations (limited overlap in resistance profiles with other non-nucleoside NS5B inhibitors in clinical trials), and compatibility with other HCV therapeutics such as interferon and ribavirin. The safety profile should permit chronic dosing for periods of at least l year.

SUMMARY OF THE INVENTION

In accordance with achieving the foregoing objects of this invention, a compound is provided having formula (1)

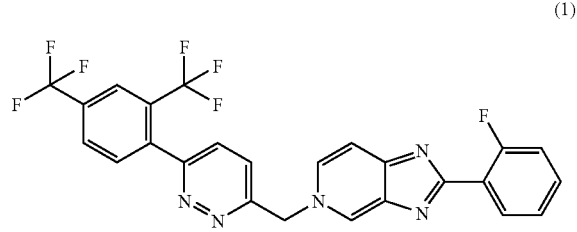

(1)

together with its salts and solvates. IUPAC: 5-({6-[2,4-bis (trifluoromethyl)phenyl]pyridazin-3-yl}methyl)-2-(2-fluorophenyl)-5H-imidazo[4,5-c]pyridine. CAS: 5H-imidazo[4,5-c]pyridine, 5-[[6-[2,4-bis(trifluorornethyl)phenyl]pyridazin-3-yl]methyl]-2-(2-fluorophenyl).

Compound (1) is useful in a method for therapy or prophylaxis of HCV infection comprising administering to a subject a therapeutic or prophylactic dose of compound (1). Another embodiment comprises the use of compound (1) for the manufacture of a medicament for the prevention or treatment of a HCV infection in a mammal (more specifically a human).

Another embodiment of this invention is a method for making a compound of formula (1)

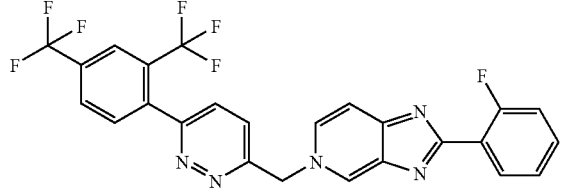

(1)

comprising (a) reacting 5-[6-chloro-pyridazin-3-ylmethyl]-2-(2-fluoro-phenyl)-5H-imidazo[4,5-c]pyridine with 2,4-bis(trifluoromethyl)phenylboronic acid in the presence of a solvent having the structure $R^1OR^2O(R^4O)_aR^3$ wherein each of $R^1$, $R^2$, $R^3$ and $R^4$ are independently selected from is C1-C6 alkyl and a is 0 or 1, and (b) recovering compound (1).

In another embodiment for the manufacture of compound (1), a method is provided comprising providing the intermediate (2)

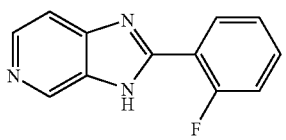

(2)

coupling 2,4-bis(trifluoromethyl)phenylboronic acid to 3-chloro-6-methylpyridazine to produce compound (2a)

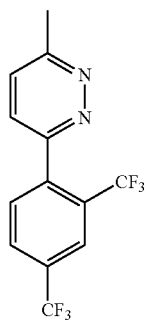

(2a)

treating compound (2a) with a chlorinating agent to produce the alkylating agent (3)

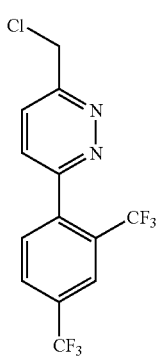

(3)

and using alkylating agent (3) to alkylate intermediate (2) under basic conditions to yield compound (1)

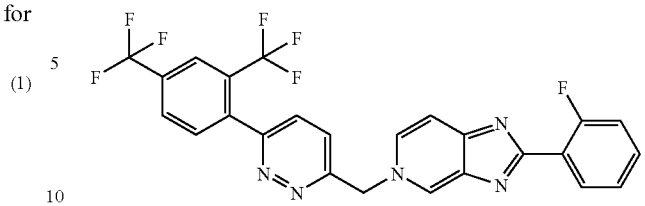

(1)

The alkylating agent (3) is new and is part of this invention, as is the same compound having methyl substitution rather than chloromethyl, or bromo, fluoro or iodo in place of chloro.

Another embodiment of this invention relates to pharmaceutical compositions of the formula (1) compound comprising at least one pharmaceutically acceptable excipient. In one embodiment the compound of formula (1) is formulated with an organic acid and optionally formulated into a pharmaceutic dosage form such as a capsule. In another embodiment, compound (1) is micronized and formulated as a suspension.

Compound (1) or the pharmaceutical compositions of this invention are employed in the treatment or prophylaxis of hepatitis C.

FIGURES

FIG. 2 is an X-ray powder diffraction pattern obtained for amorphous form compound (1) Research Lot 6, obtained by the method of Example 1a.

FIG. 4 shows a DSC thermogram obtained for amorphous form compound (1) Research Lot 6, 5° C./min scan, obtained by the method of example 1a.

DETAILED DESCRIPTION OF THE INVENTION

Figure 1:
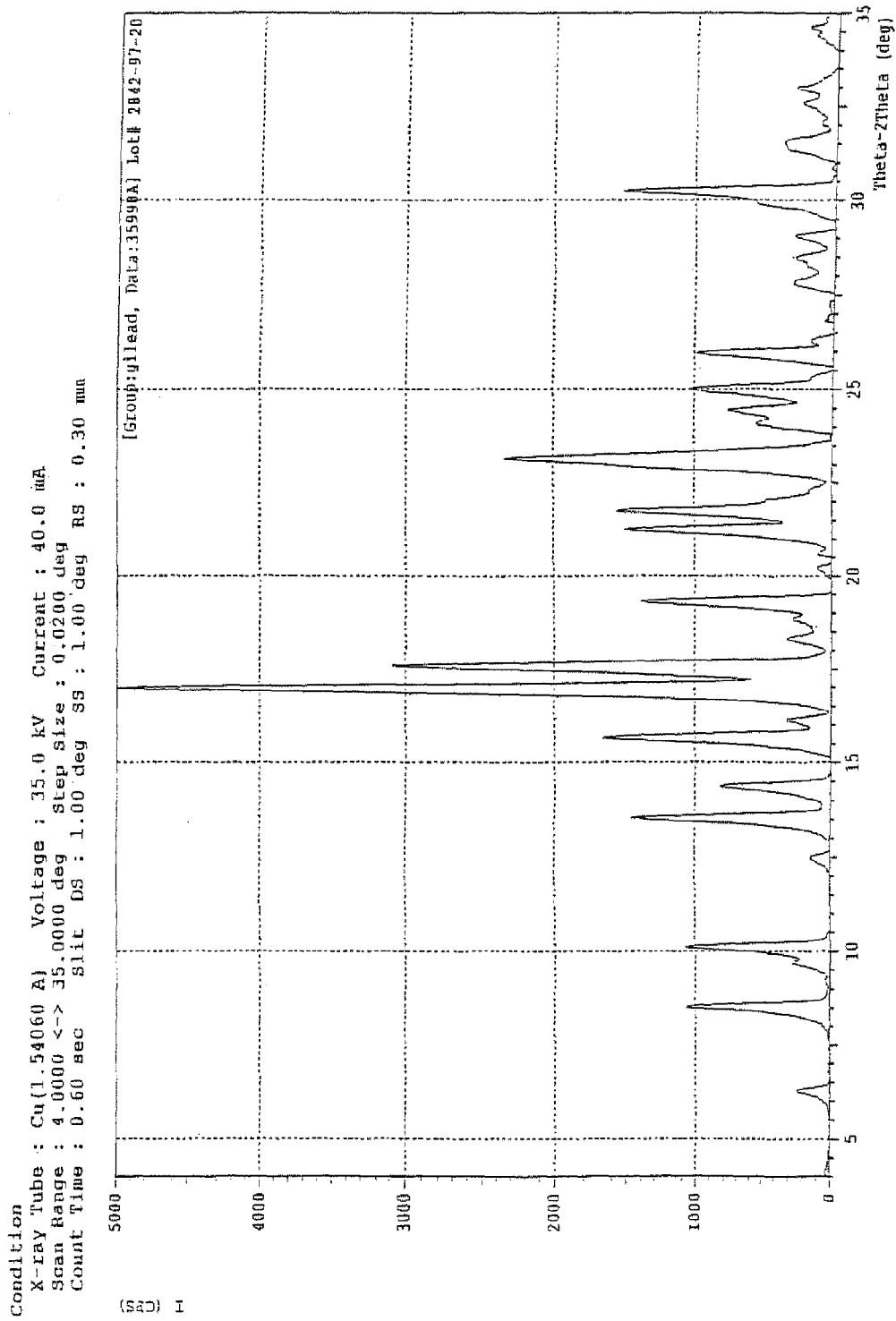
FIG. 1 depicts an X-ray powder diffraction pattern obtained for crystal form compound (1) reference standard obtained by the method of example 1b.

The therapeutic compound of this invention is administered to a subject mammal (including a human) by any means well known in the art, i.e. orally, intranasally, subcutaneously, intramuscularly, intradermally, intravenously, intra-arterially, parenterally or by catheterization in a therapeutically effective amount, i.e., an HCV-inhibiting amount or an HCV-replication inhibiting amount. This amount is believed to be an amount that ensures a plasma level of about 100 nM, 3 times the protein adjusted EC90. This ordinarily is expected to be achieved by oral administration of about 0.5—about 5 mg/kg, typically about 0.7 to 2.2 mg/kg, most ordinarily about 1.2 mg/kg bodyweight for humans.

The optimal dosage of the compound of this invention will depend upon many factors known to the artisan, including bioavailability of the compound in a given formulation, the metabolism and distribution of the compound in the subject, the fasted or fed state of the subject, selection of carriers and excipients in the formulation, and other factors. Proper dosing typically is determined in the preclinical and clinical settings, and is well within the skill of the ordinary artisan. The therapeutically effective amount of the compound of this invention optionally is divided into several sub-units per day or is administered daily or in more than one day intervals, depending upon the nature of the infection, the patient's general condition and the formulation of the compound of this invention. Generally, the compound is administered twice daily.

The compound of this invention is employed in concert with other agents effective against HCV infections. They optionally are administered separately in a course of therapy, or are combined with compound (1) in a unitary dosage form such as tablet, iv solution or capsule. Such other agents include, for instance, interferon-alpha, ribavirin, and/or compounds falling within the disclosures of EP1162196, WO 03/010141, WO 03/007945, WO 00/204425 and/or WO 03/010140 (and other filings within their patent families). Other agents for administration in a course of therapy with the compound of this invention include compounds now in clinical trials, in particular HCV protease inhibitors such as VX-950 (Vertex Pharmaceuticals), SCH 5030347 (Schering Plough) and BILN-2061 (Boehringer Ingelheim), nucleoside HCV inhibitors such as NM283, NM107 (both Idenix/Novartis) and R1626 (Hoffmann-LaRoche), and non-nucleoside HCV inhibitors including HCV-086 and -796 (both ViroPharma/Wyeth). Supplementary antiviral agents are used in conventional amounts, although if the efficacy of the compound of this invention and the supplementary compound are additive then the amounts of each active agent optionally are commensurately reduced, and more so if the agents act synergistically. In general, however, the agents are used in their ordinary active amounts in unitary combination compositions.

Co-administered agents generally are formulated into unitary compositions with the compound of this invention so long as they are chemically compatible and are intended to be administered by the same route. If not, then they optionally are provided in the form of a medical kit or package containing the two agents in separate repositories or compartments.

The compound of this invention is provided as the free base or as a salt. Salts typically are prepared by acid addition of organic and/or inorganic acids to the free base. Examples include (1) inorganic acids such as hydrohalogen acids, e.g. hydrochloric or hydrobromic acid, sulfuric acid, nitric acid, phosphoric acid and sulfamic acids; or (2) organic acids such as acetic, propanoic, hydroxyacetic, benzoic, 2-hydroxypropanoic, 2-oxopropanoic, lactic, fumaric, tartaric, pyruvic, maleic, malonic, malic, salicylic (e.g. 2-hydroxybenzoic), p-aminosalicylic, isethionic, lactobionic, succinic, oxalic and citric acids; organic sulfonic acids, such as methanesulfonic, ethanesulfonic, benzenesulfonic, p-toluenesulfonic, C1-C6 alkylsulfonic, benzenesulfonic, p-toluenesulfonic, and cyclohexanesulfamic acids. Typical salts are the chloride, sulfate, bisulfate, mesylate, besylate, esylate, phosphate, oxalate, maleate, succinate, citrate, malonate, and/or fumarate. Also included within the scope of this invention are the salts of the compound of this invention with one or more amino acids, typically naturally-ocurring amino acids such as one of the amino acids found in proteins. The acidic counterion desirably is physiologically innocuous and non-toxic or otherwise pharmaceutically acceptable, unless the salt is being used as an intermediate in preparation of the compounds whereupon toxicity is not relevant. Ordinarily, compound (1) will be administered as the free base, but suitable salts include mesylate (methanesulfonic acid) and HCl.

The compound of this invention includes the solvates formed with the compound of this invention or their salts, such as for example hydrates, alcoholates and the like.

The pharmaceutical compound of this invention optionally is formulated with conventional pharmaceutical carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (2005) and include ascorbic acid and other antioxidants, chelating agents such as EDTA, carbohydrates such as dextrin, hydroxyalkylcellulose, hydroxyalkylmethylcellulose and/or organic acids such as oleic acid or stearic acid.

The term "pharmaceutically acceptable carrier" as used herein means any material or substance formulated with the active ingredient in order to facilitate its preparation and/or its application or dissemination to the site to be treated. Suitable pharmaceutical carriers for use in the compositions of this invention are well known to those skilled in the art. They include additives such as wetting agents, dispersing agents, adhesives, emulsifying agents, solvents, glidants, coatings, antibacterial and antifungal agents (for example phenol, sorbic acid, chlorobutanol), and isotonic agents (such as sugars or sodium chloride), provided that the same are consistent with pharmaceutical practice, i.e. they are not toxic to mammals.

The pharmaceutical compositions of the present invention are prepared in any known manner, for instance by homogeneously mixing, coating and/or grinding the active ingredients in a one-step or multi-step procedure, with the selected carrier material and, where appropriate, other additives such as surface-active agents. Compositions containing the compound of this invention formulated into microspheres (usually having a diameter of about 1 to 10 gm) are useful as controlled or sustained release formulations.

In one optional formulation, compound (1) is comminuted to a finely divided form, typically to an average particle size at any point within the range of about 1-20 microns. The product of example 1b is crystalline needles and exhibits a range of crystal sizes, typically about 25-40 microns. This optionally is micronized in a Jet mill-00 at about 60-80 psi to obtain particles of about 3-4 microns and having surface area of about 7-8 square meters/g. However, the starting crystal sizes will vary from lot to lot and the degree of micronization is a matter of choice. Accordingly, micronized compound (1) is simply defined as crystal or amorphous compound (1) that has been subject to a micronization process such as the exemplary one described here. Neither the size nor surface area of the resulting particles is critical. The micronized compound (1) is suspended in aqueous solution, optionally aided by a suspending agent, emulsifiers and/or surfactant as further described below.

Typically, the pharmaceutical formulation is a solubilized form of compound (1) where compound (1) is dissolved in an appropriate solvent or solubilizing agent, or combinations thereof. Compound (1) solubilized in organic solvent is useful as an intermediate for the preparation of crystalline compound (1), but typically it is solubilized in a pharmaceutically acceptable excipient for administration therapeutically or prophylactically.

Suitable solutions of compound (1) for pharmaceutical preparations include water together with various organic acids (typically C4-C24) usually fatty acids like capric, oleic, lauric, capric, palmitic and/or myristic acid. The fatty acids are optionally saturated or unsaturated, or mixtures thereof. In addition, polyethylene glycols (PEGs) and/or short, medium, or long chain mono, di, or triglycerides are employed supplementary to, or in place of, the organic acids. Pegylated short, medium or long chain fatty acids optionally also are used in the same fashion.

The most common organic acids are the carboxylic acids whose acidity is associated with the carboxyl group —COOH. Sulfonic acids, containing the group $OSO_3H$, are relatively stronger acids for use herein. In general, the acid desirably contains a lipophilic domain. Mono- or di-carboxylic acids are suitable.

Suitable surface-active agents optionally are used with any of the formulations of this invention (any one or more of the following agents, typically any one of them). Such agents also are known as emulgents or emulsifiers, and are useful in the pharmaceutical compositions of the present invention. They are non-ionic, cationic and/or anionic materials having suitable emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures. Aqueous emulsions with such agents are within the scope of this invention.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8-C22 alkyl radical (e.g. cetyl, lauryl, palmityl, myristyl and oleyl) and, as further substituents, unsubstituted or halogenated lower alkyl, benzyl and/or hydroxy-lower alkyl radicals.

A more detailed description of surface-active agents suitable for this purpose is found in "McCutcheon's Detergents and Emulsifiers Annual" (MC Publishing Crop., Ridgewood, N.J., 1981), "Tensid-Taschenbucw", 2nd ed. (Hanser Verlag, Vienna, 1981) and "Encyclopaedia of Surfactants," (Chemical Publishing Co., New York, 1981).

The compound of this invention is administered by any route appropriate to the condition to be treated, such as oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient, but is generally oral.

Formulations of the compound of this invention for oral administration usually are presented as discrete units such as capsules, cachets or tablets each containing a predetermined amount of the active ingredient; as a powder or granular form; as a solution or suspension in an aqueous liquid or a non-aqueous liquid; or as an oil-in-water liquid emulsion or a water-in-oil liquid emulsion. The compound of this invention optionally is presented as a bolus, electuary or paste.

A tablet is made by compression or molding, optionally with one or more accessory ingredients. Compressed tablets are prepared by compressing in a suitable machine the compound of the invention in a free-flowing form such as a powder or granules, optionally mixed with a binder, lubricant, inert diluent, preservative, surface active and/or dispersing agent. Molded tablets typically are made by molding in a suitable machine a mixture of the powdered compound moistened with an inert liquid diluent. The tablets may optionally be coated or scored and may be formulated so as to provide slow or controlled release of the active ingredient therein.

The formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the compound is employed with a paraffinic or a water-miscible ointment base. Alternatively, the compound is formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention is constituted from known ingredients in a known manner. While this phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by aerosol or powder inhalers, of which numerous examples are available. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations are presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compound of this invention optionally is formulated into controlled release compositions in which the release of the compound is controlled and regulated to allow less frequency dosing or to improve the pharmacokinetic or toxicity profile of the invention compound. Controlled release compositions are prepared in accord with known methods, many of which involve formulating the active compound with one or more polymer carriers such a polyester, polyamino acid, polyvinyl pyrrolidone, ethylene-vinyl acetate copolymer, methylcellulose, carboxymethylcellulose and/or protamine sulfate. The rate of drug release and duration of action optionally is controlled by incorporating the active ingredient into particles, e.g. microcapsules, of a polymeric substance such as hydrogels, polylactic acid, hydroxymethylcellulose, polymethyl methacrylate and the other above-described polymers. Also suitable are colloid drug delivery systems such as liposomes, microspheres, microemulsions, nanoparticles, nanocapsules and so on. Depending on the route of administration, the pharmaceutical composition, e.g., tablets, may require protective coatings.

The invention will be more fully appreciated by reference to the following examples, which are to be considered merely illustrative and not limiting the scope of the invention as claimed.

EXAMPLE 1a

Synthesis of 5-({6-[2,4-bis(trifluoromethyl)phenyl]pyridazin-3-yl}methyl)-2-(2-fluorophenyl)-5H-imidazo[4,5-c]pyridine In this method, dimethoxyethane or its related solvents, all having the general formula $R^1OR^2O(R^4O)_aR^3$ wherein each of $R^1$, $R^2$, $R^3$ and $R^4$ are independently selected from C1-C6 alkyl and a is 0 or 1, have been found to be particularly advantageous over the conventional solvent DMF. Typically, each of $R^1$, $R^2$, $R^3$ and $R^4$ are independently $C_1$-$C_2$ alkyl and usually a is 0. $C_1$-$C_6$ alkyl includes fully saturated primary, secondary or tertiary hydrocarbon groups with 1 to 6 carbon atoms and thereby includes, but is not limited to methyl, ethyl, propyl, butyl, etc.

Step 1

| Compound | MW | Amount | mmoles | Equivalents |
|---|---|---|---|---|
| SM | 128.56 | 5 g | 38.9 | 1 |
| TCCA | 232.41 | 3.62 g | 15.6 | 0.4 |
| CHCl$_3$ | | 130 ml | | |

To a solution of the commercially available starting material (SM) in CHCl$_3$, trichloroisocyanuric acid (TCCA) was added at 60° C. Then the solution was stirred for 1.5 hrs., cooled down and filtered with HiFlo-Celite. The filtrate was concentrated and dried with vacuum. The yield was 5.037 g.

Step 2

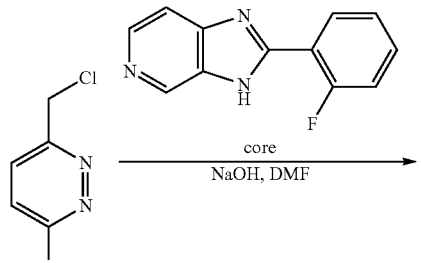

| Compound | MW | Amount | mmoles | Equivalents |
|---|---|---|---|---|
| S.M. | 163 | 5.073 g | 31.12 | 1 |
| Core | 213.2 | 6.635 g | 31.12 | 1 |
| NaOH (10%) | 40 | 1.245 g | 31.12 | 1 |
| DMF |  | 320 ml |  |  |

To a solution of core (obtained as described in literature in DMF (dimethylformamide), NaOH was added. Then SM for this step (obtained from step 1) was dissolved in DMF (20 ml) and added to the solution slowly. The reaction was stirred for 3 hrs, was diluted with water and extracted with EtOAc. The organic layer was dried with Na$_2$SO$_4$. The solvent was removed and the product recrystallized with DCM (dichloromethane). The yield was 5.7 g.

Step 3

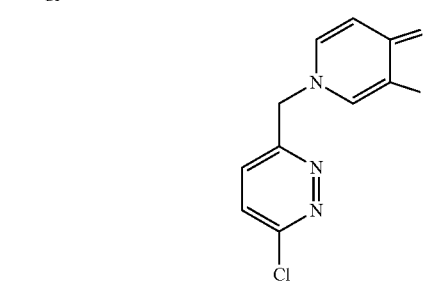

A

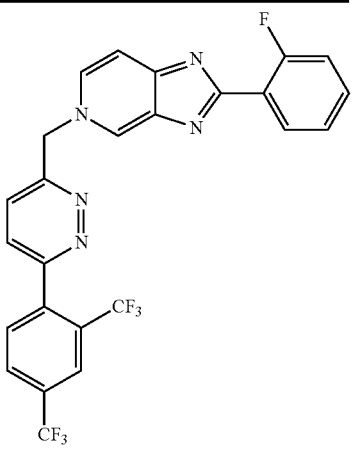

| Compound | MW | Amount | Moles | Equivalents |
|---|---|---|---|---|
| A | 453.79 | 95 mg | 0.209 | 1 |
| DME |  | 500 ul |  |  |
| 2N aq. Na$_2$CO$_3$ |  | 313 ul | 0.626 | 3 |
| 2,4-bisCF$_3$-phenylboronic acid | 257.93 | 80.9 mg | 0.313 | 1.5 |
| Pd(PPh$_3$)$_4$ | 1155 | 12 mg | 0.0104 | 0.05 |

Compound A was dissolved in dimethoxyethane (DME). To this solution was added 2,4-bis(trifluromethyl)phenylboronic acid and a 2N aq. Na$_2$CO$_3$ solution. To the resulting biphasic mixture was added Pd(PPh$_3$)$_4$ and the reaction was then heated at 80° C. for 72 hrs. The reaction was cooled to room temperature and filtered through Celite and the Celite washed with EtOAc. The filtrate was concentrated in vacuo. The residue was purified on 6 g SiO2 using MeOH/CH2Cl2 to elute compound. The compound thus obtained was contaminated with PPh$_3$(O). The product was repurified on a 1 mm Chromatotron plate with 0 to 5% MeOH/CH$_2$Cl$_2$ in 1% steps. The pure fractions were combined and concentrated in vacuo, then dried on high vacuum for 12 hrs. 11.8 mg of the free base of compound (1) was obtained with no PPh$_3$ contamination.

$^1$H NMR (300 MHz, CD$_3$OD)

6.20 (s, 2)

7.32 (m, 3)

7.52 (m, 1)

7.78 (d, 1)

7.89 (d, 1)

7.95 (s, 2)

8.15 (m, 3)

8.35 (d, 1)

9.12 (s, 1)

LC/MS M+H=518

EXAMPLE 1b

Synthesis of 5-({6-[2,4-bis(trifluoromethyl)phenyl]pyridazin-3-yl}methyl)-2-(2-fluorophenyl)-5H-imidazo[4,5-c]pyridine This example is directed to an additional method for making compound (1), employing the following schemes.

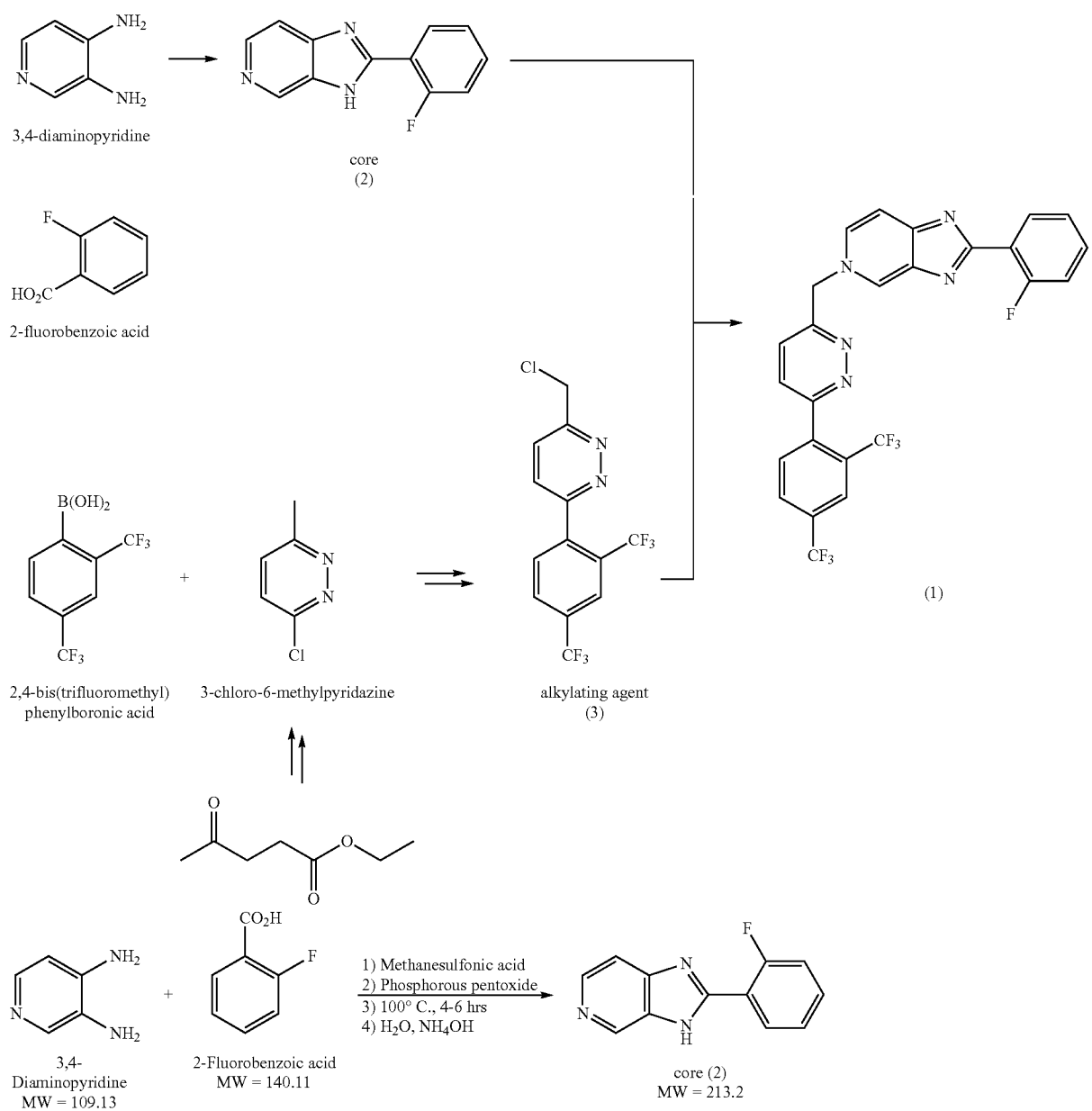

Scheme 1

Methanesulfonic acid was added to 2-fluorobenzoic acid in a reactor with active cooling keeping T≦50° C. 3,4-Diaminopyridine was then added portionwise to this cooled slurry, keeping T≦35° C. The contents of the reactor were then heated to 50° C. Phosphorus pentoxide was added in a single charge. The reaction was then heated at 90-110° C. for at least 3 hours. The reaction was sampled for completion by HPLC analysis. The reaction was cooled to ambient temperature and water was added portionwise slowly to quench the reaction. The reaction was then diluted with water. In solubles were removed by filtration. The pH of the filtrate was adjusted to 5.5-5.8 with ammonium hydroxide. The reaction was allowed to self-seed and granulate for ~4 hours at ambient temperature. The pH was then adjusted to 8.0-9.3 with ammonium hydroxide. The slurry was held at ambient temperature for at least 2 hours. The solids were isolated by filtration and washed with water, followed by IPE. The wet cake was dried in vacuo at not more than 60° C. until ≦1% water remains. The dry product is core (2).

| Summary of Materials | M.W. | Wt. Ratio | Mole ratio |
|---|---|---|---|
| 3,4-Diaminopyridine | 109.13 | 1.0 | 1.0 |
| 2-Fluorobenzoic acid | 140.11 | 1.4 | 1.1 |
| Methanesulfonic acid | 96.1 | 7.0 | 8.0 |
| Phosphorus pentoxide | 141.94 | 1.3 | 1.0 |
| Water | 18.02 | 40 | — |
| Isopropyl ether | 102.17 | 5.0 | — |
| Ammonium hydroxide | 35.09 | ~10 | — |

Scheme 1a

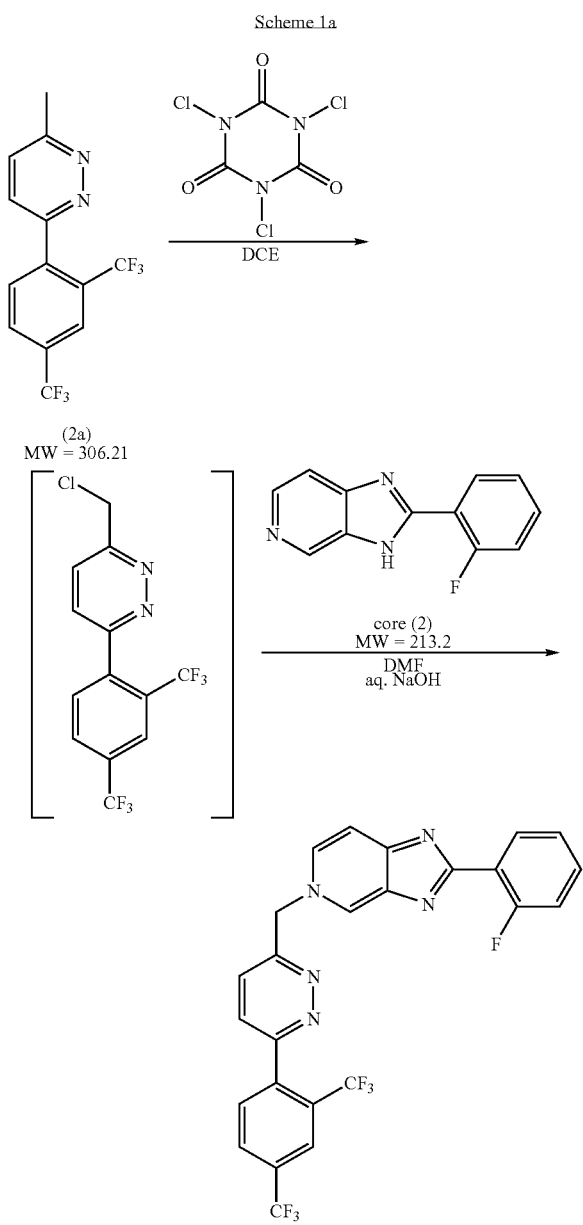

A solution of compound (2a) in 1,2-dichloroethane was heated to 40-45° C. Trichloroisocyanuric acid was added and the mixture was heated at 60-70° C. for at least 2 hours. The reaction was sampled for completion by HPLC analysis. The reaction was cooled to ambient temperature. Celite was added to absorb insolubles, then solids were removed by filtration. The filtrate was washed with 0.5 N sodium hydroxide solution. The organic layer was concentrated to lowest stirrable volume and displaced with DMF. Core (2) and 10% aqueous sodium hydroxide solution were added. The reaction was stirred at ambient temperature for at least 8 hours. The reaction was sampled for completion by HPLC analysis. An additional 10% charge of 10% sodium hydroxide solution was added to the reaction. The reaction was then charged into water to isolate the crude product. After granulating for at least 1 hour, the solids were isolated and washed with water and isopropyl ether. Ethyl acetate was added and refluxed (internal T=70-77° C.) for 1-5 hours to dissolve product, then cooled to 18-23° C. slowly over 4-8 hours. The reactor contents were agitated at 18-23° C. for 8-20 hours and solids collected by filtration and rinsed with ethyl acetate. Low melt (i.e., DSC about 220 degrees C.) amorphous compound (1) was discharged. Amorphous compound (1) was dissolved in ethyl acetate by heating at reflux (internal T=70-77° C.) for 1-5 hours. Water content is controlled to about 0.2% by azeotropically removing water (with ethyl acetate the upper limit on water content is about 0.6% by weight; at about 0.9% by weight water the amorphous material will reprecipitate and crystals will not be obtained). The reactor contents are cooled slowly to 18-23° C. over 4-8 hours, then agitated at 18-23° C. for 8-20 hours and solids collected by filtration. The solids were rinsed with ethyl acetate and dried in vacuo at not more than 60° C. to obtain the dry crystalline compound (1).

| Summary of Materials | M.W. | Wt. Ratio | Mole ratio |
|---|---|---|---|
| 3-chloro-6-methylpyridazine | 128.56 | 1.0 | 1.0 |
| 2,4bis(trifluromethyl)phenylboronic acid | 257.93 | 4.0 | 2.0 |
| X-Phos | 476.72 | 0.18 | 0.05 |
| Palladium acetate | 224.49 | 0.04 | 0.025 |
| 1,2-Dimethoxyethane | 90.12 | 16.7 | — |
| Potassium carbonate | 138.21 | 2.15 | 2.0 |
| Water | 18.02 | 7.8 | — |
| Copper iodide | 190.45 | 0.037 | 0.025 |
| Celite | — | 0.25 | — |
| Heptane | 100.2 | 22.4 | — |

Nuclear Magnetic Resonance ($^1$H-, $^{13}$C-, and $^{19}$F-NMR) Spectra

Nuclear magnetic resonance (NMR) spectra of compound (1) is consistent with the proposed structure. The $^{13}$C, $^{19}$F, and $^1$H-NMR spectra of compound (1) in DMSO-$d_6$ were measured using a Varian UnityInova-400 FT-NMR spectrometer. Spectra are shown in the table below. The NMR chemical shift assignments were established using 2D correlation experiments (COSY, HSQC, HMBC and HSQCTOCSY).

$^1$H and $^{13}$C-NMR chemical shift assignments for Compound (1) reference standard

| Atom | δC/ppm (DMSO-$d_6$) | δF/ppm (DMSO-$d_6$) | δH/ppm (DMSO-$d_6$) |
|---|---|---|---|
| 1A | 140.16 | | |
| 2A | 128.32 (q$^a$, J$_{CF}$ = 32 Hz) | | |
| 3A | 123.61, m | | 8.24 (m, 1 H) |
| 4A | 130.27 (q, J$_{CF}$ = 34 Hz) | | |
| 5A | 129.54 (q, J$_{CF}$ = 3 Hz) | | 8.22 (m, 1 H) |
| 6A | 133.36 | | 7.88 (m, 1 H) |
| 7A | 123.20 (q, J$_{CF}$ = 273 Hz) | −56.4$^b$ | |
| 8A | 123.02 (q, J$_{CF}$ = 275 Hz) | −62.0$^b$ | |
| 1B | 158.76 | | |
| 2B | 128.16 | | 8.01 (d, 1 H, J = 8.4 Hz) |
| 3B | 126.20 | | 7.95 (d, 1 H, J = 8.8 Hz) |
| 4B | 157.70 | | |
| 5B | 60.49 | | 6.17 (s, 2 H) |
| 2C | 131.86 | | 8.31 (m, 1 H) |
| 3C | 112.63 | | 7.86 (m, 1 H) |
| 4C | 155.44 | | |
| 6C | 168.11 (d, J$_{CF}$ = 6 Hz) | | |
| 8C | 145.08 | | |
| 9C | 133.06 | | 9.25 (s, 1 H) |
| 1D | 123.11 (d, J$_{CF}$ = 10 Hz) | | |

-continued

| Atom | δC/ppm (DMSO-d$_6$) | δF/ppm (DMSO-d$_6$) | δH/ppm (DMSO-d$_6$) |
|---|---|---|---|
| 2D | 160.46 (d, J$_{CF}$ = 254 Hz) | −111.7 | |
| 3D | 116.59 (d, J$_{CF}$ = 22 Hz) | | 7.29 (m, 1 H) |
| 4D | 130.84 (d, J$_{CF}$ = 8 Hz) | | 7.46 (m, 1 H) |
| 5D | 124.13 (d, J$_{CF}$ = 4 Hz) | | 7.31 (m, 1 H) |
| 6D | 131.72 (d, J$_{CF}$ = 2 Hz) | | 8.35 (m, 1 H) |

$^a$multiplicity, s: singlet, d: doublet, q: quartet, m: multiplet
$^b$interchangeable signals

Differential Scanning Calorimetry

Compound (1) samples made according to the methods of examples 1a (Research lot 6)) and 1b (remaining samples) were subjected to measurement using a Differential Scanning Calorimetry (DSC) apparatus (DSC2010, manufactured by TA Instruments Corporation), under nitrogen atmosphere, sample weight 5±1 mg, temperature rise rate: either 1° C. per min, 5° C. per min or 10° C. per min, open aluminum pan, and indium standard as a reference. The enthalpy, extrapolated onset temperature and apex temperature at an endothermic peak on the obtained DSC curve were determined.

The DSC results for representative Compound (1) batches are summarized in Table 1. When the crystal form of Compound (1) produced by the example 1b method was subjected to DSC scan at 1° C./min, the enthalpy of the endothermic peak is about 81 J/g±1 J/g, and the extrapolated onset temperature is 233.2° C.±2.0 The apex of the endothermic peak is 233.9° C.±3.0° C.

TABLE 1

Example DSC values obtained for Compound (1) batches

| | 10° C./min scan | | 1° C./min scan | | |
|---|---|---|---|---|---|
| | peak onset | main peak | peak onset | main peak | Enthalpy (J/g) |
| Compound (1)Ref Std | 235.8 | 237.2 | 233.7 | 234.6 | 89.5 |
| Compound (1)-A-1 | n/a | n/a | 234.8 | 234.0 | — |
| Compound (1)-B-1 Crop 1 | 235.2 | 237.4 | 231.6 | 232.2 | 78.5 |
| Compound (1)-B-1 Crop 2 | 236.1 | 238.5 | 234.3 | 235.6 | 80.9 |
| **Research Lot 6 | 220.2 | 221.3 | pending | pending | 39.1 |

Note:
All ° C. exceept for enthalpy
**5° C./min scan reported for Lot 6

X-Ray Powder Diffractometry

Samples made by methods 1a and 1b were analyzed in the as received condition, only mixing with a spatula prior to analysis. A sample was fixed to an aluminum cell, and the measurement was performed using an X-ray powder diffractometer (XRD-6000, Shimadzu Lab X, manufactured by Shimadzu Corporation, X-ray source: Cu—Kα1 ray, tube voltage: 35 kV, tube electric current: 40 mA, scan speed: 2° per min, continuous scan mode, sampling pitch: 0.02°, scan range: 4-35°, β axis rotation: 60 rpm).

Non-micronized, ascicular compound (1) crystals obtained by the example 1b method have an X-ray powder diffraction pattern having characteristic diffraction peaks at diffraction angles 2θ (°) of 13.46, 15.59, 16.90, 17.48, 23.05 and 30.15 as measured by X-ray powder diffractometer (FIG. 1). Note that the non-micronized "high melt" 235° C. melt ascicular crystal form of compound (1) tested in this example shows some effects due to preferred orientation and particle size. As a result, FIG. 1 should be considered merely exemplary because varying the crystal size and orientation will change the magnitude of the peaks in the plot. Additionally, the diffraction peak value at the above mentioned diffraction angle 2θ (°) may show slight measurement error due to the measurement instrument or measurement conditions and the like. Typically, the measurement error generally is within the range of about ±0.3. The specification for the Shimadzu XRD-6000 is ±0.04. In addition, some variation in peak positions can be expected due to product and experimental variation, so they must be considered approximate.

Figure 2:
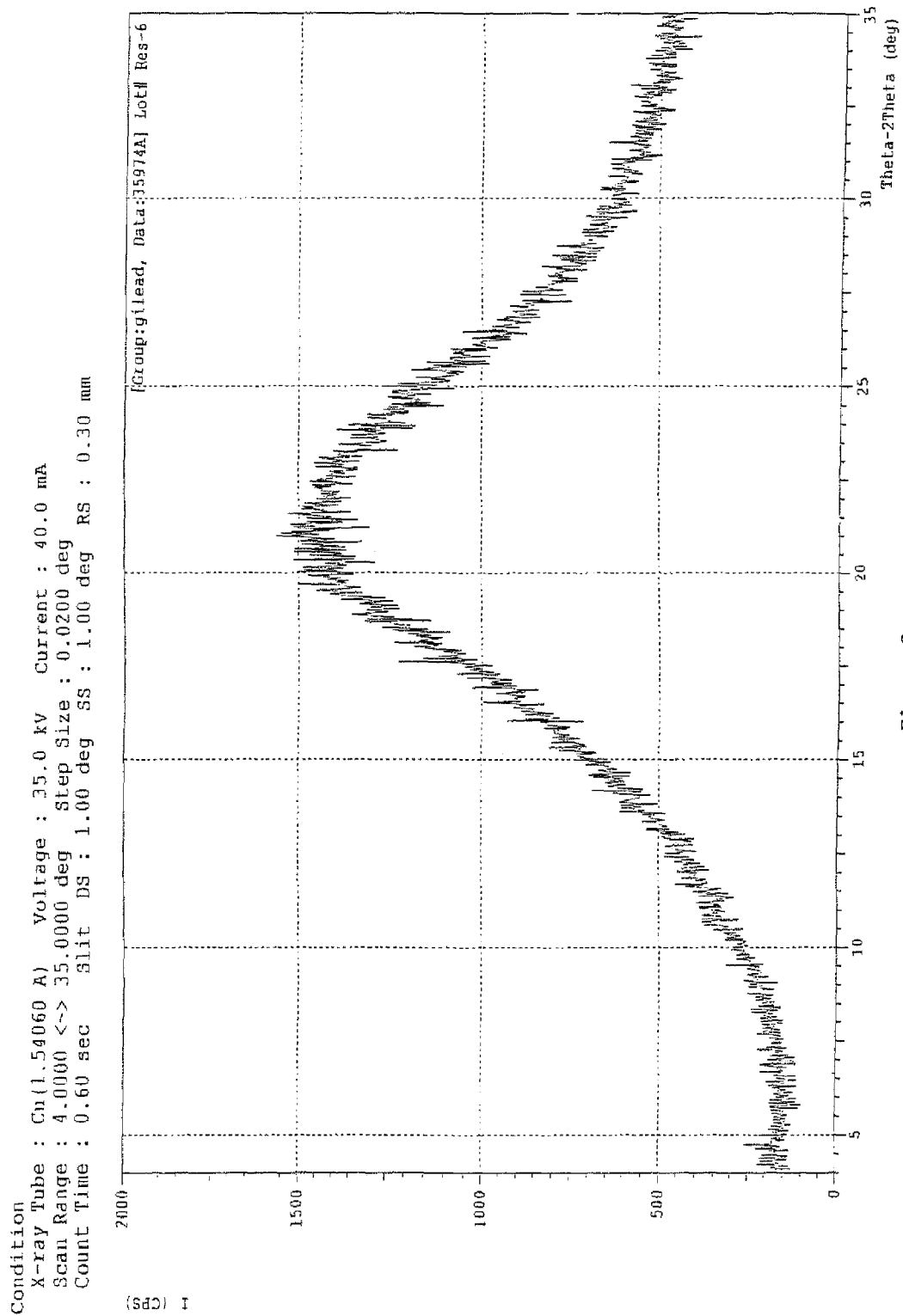
Figure 3:
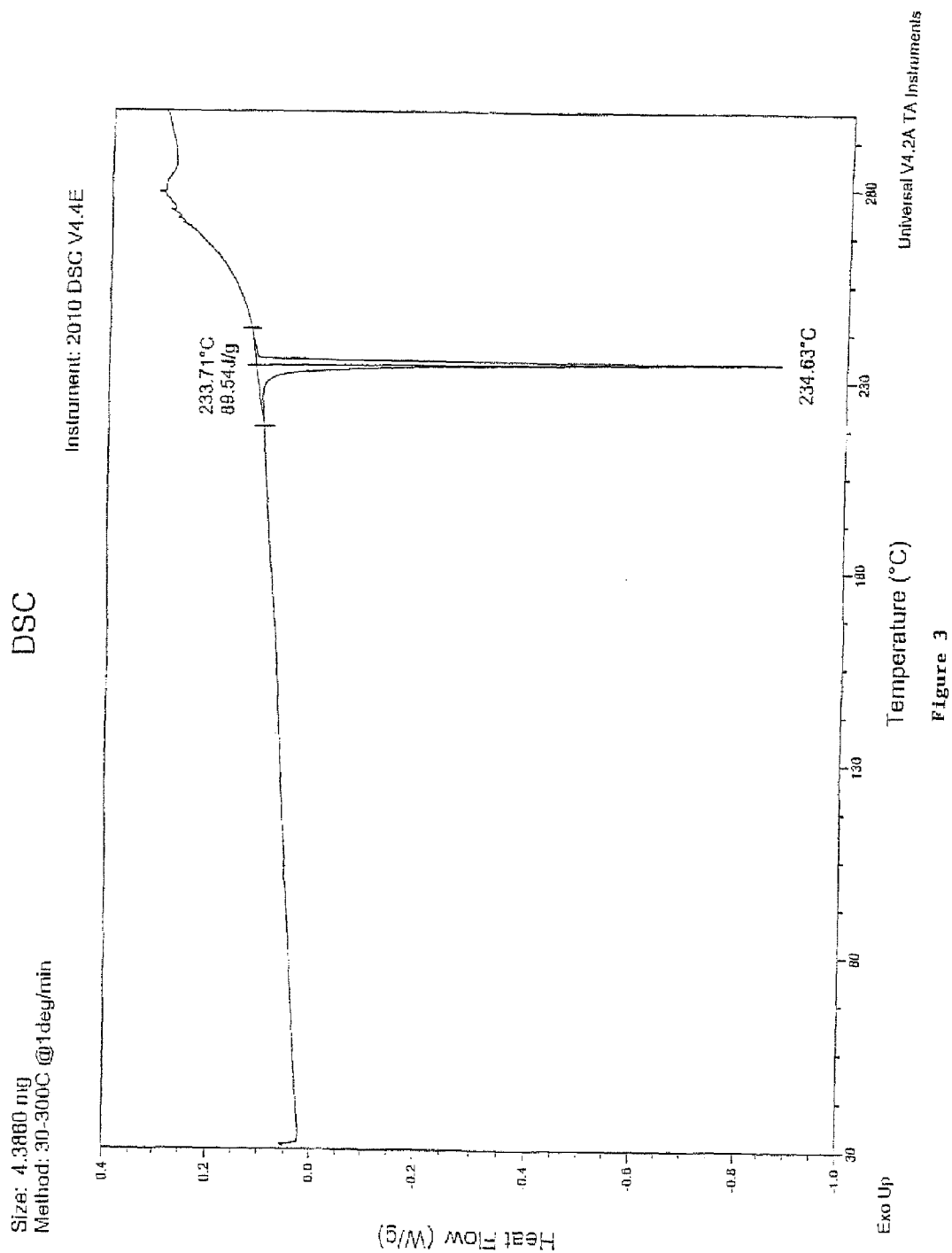
FIG. 3 illustrates a DSC thermogram obtained for crystal form compound (1) reference standard, 1° C./min scan, obtained by the method of example 1b.
Figure 4:
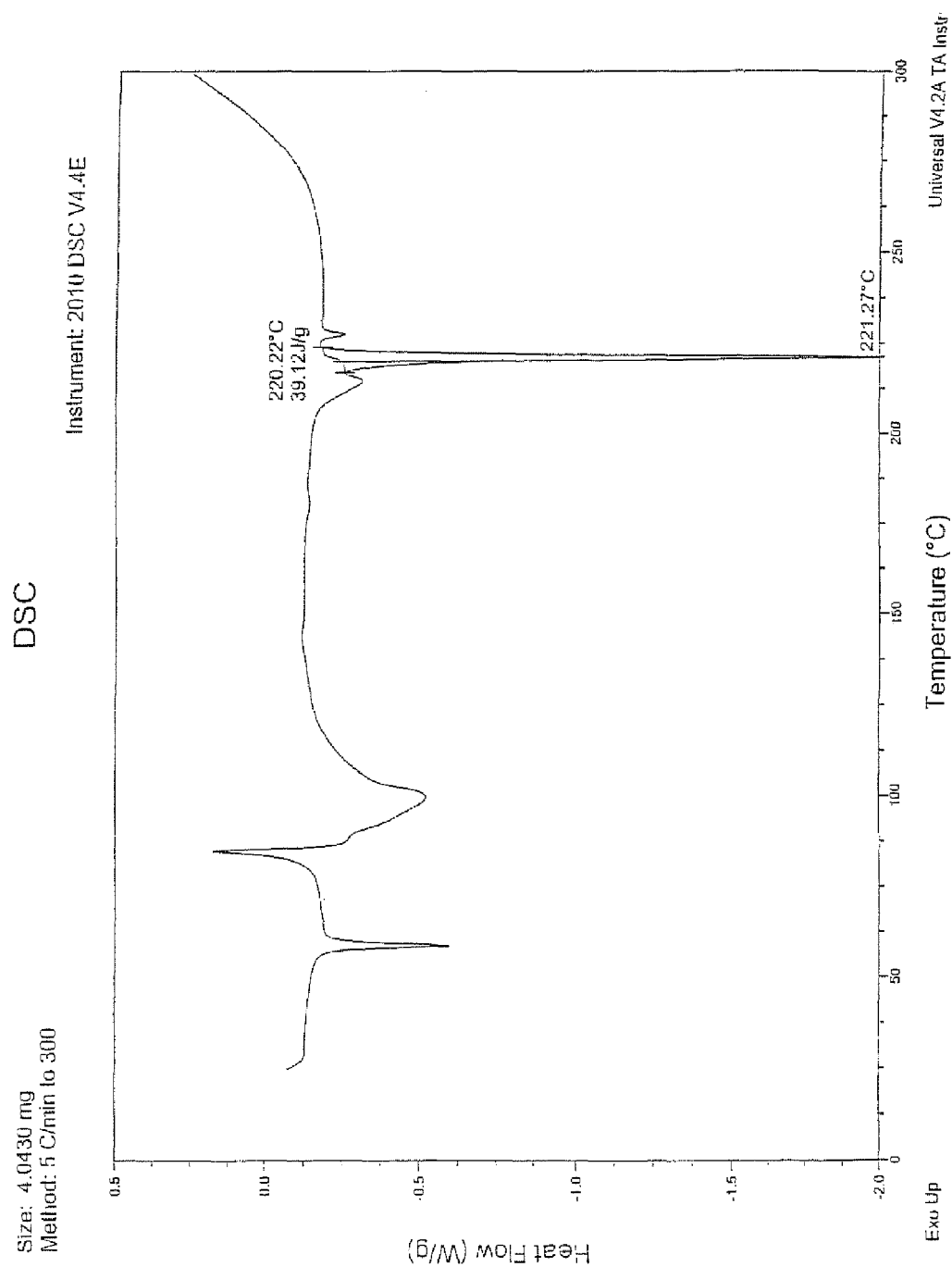

The 220° C. "low melt" solid state form of compound (1) comprised by product made according to the example 1a method (or in the method 1b prior to the reslurry step) gives an X-ray powder diffraction pattern consistent with amorphous material (FIG. 2).

The product of this method 1b is crystalline compound (1) substantially free of amorphous compound. It exhibits an endothermic onset at about 235° C. in differential scanning calorimetry (DSC) profile. It exhibits an approximate heat of fusion (DH$_f$) of 81 J/g (42 KJ/mole)±1 J/g. Crystalline compound (1) is produced substantially free of amorphous compound (1) by reslurring the reaction product in substantially anhydrous crystallization solvent, as described above. The crystallization solvent is any solvent or cosolvent mixture in which compound (1) will dissolve. Suitable solvents include isopropyl acetate/ethyl acetate cosolvent, or ethyl acetate alone.

Substantially anhydrous solvent is defined as solvent containing a sufficiently small amount of water that the product compound (1) composition according to method 1b contains crystalline compound (1) and less than about 40%, ordinarily less than about 30, 20, 10, 5, 3, 2 or 1% by weight of any other form of compound (1) (including amorphous compound (1)) in the total of all forms of compound (1) in the product composition.

In general, substantially anhydrous solvent will contain less than about 0.5% -0.6% by weight of the crystallization solvent as water, although the amount of permitted water will vary based on the objectives of the process. For example, more water can be present if the desired product is permitted to contain the greater proportions of amorphous compound (1). The determination and selection of the amount of permitted water is entirely within the skill of the artisan and will depend upon a number of factors, including the nature and identity of the solvent, the presence of agents for scavenging water, the temperature of the reaction and other conditions.

Compound (1) by example 1b typically exhibits intrinsic solubility of 0.7 micrograms/ml, a pKa of 5.8, log P of 2.8; and geometric mean (3 lots) pH solubility profile at pH 2 of 458 micrograms/ml and at pH 7.3, 0.7 micrograms/ml. Geometric mean solubility (3 lots) in simulated intestinal fluids (fasted: pH 6.4, 0.75 mM lecithin, 3 mM sodium taurocholate, 270 mOsmol; fed: pH 5.0, 3.75 mM lecithin, 15 mM sodium taurocholate, 635 mOsmol) were 19.1 micrograms/ml (fasted) and 122 micrograms/ml (fed).

Measured parameters vary from lot to lot, so all of the foregoing parameters except molecular weight should be considered to be approximate.

Titration with acids revealed higher solubility with mesylate (>20 mg/ml) compared to the chloride (about 0.6 mg/mL) or sulfate (about 0.5 mg/mL) counterions.

EXAMPLE 2

Formulation of Compound (1)

Compound (1) formulations are made on a weight by weight basis to achieve 10% w/w active. To make 12 kg solution, exemplary quantitative compositions of compound (1) capsules, 20 mg and 40 mg are listed below.

Quantitative composition of Compound (1) capsules, 20 mg and 40 mg

| Components | % w/w | Capsule Unit Formula (mg/unit) 20 mg | 40 mg | Compendial Reference | Function |
|---|---|---|---|---|---|
| Compound 1 | 10.00 | 20.0 | 40.0 | None | Active ingredient |
| Oleic Acid | 84.55 | 169.1 | 338.2 | NF | Solvent |
| Polysorbate 80 | 5.00 | 10.0 | 20.0 | NF | Surfactant |
| Butylated Hydroxytoluene (BHT) | 0.10 | 0.2 | 0.4 | NF | Antioxidant |
| Butylated Hydroxyanisole (BHA) | 0.35 | 0.7 | 1.4 | NF | Antioxidant |
| Capsule Sealing Solution$^a$ | | | | | Capsule sealant |
| Ethanol | —$^b$ | —$^b$ | —$^b$ | USP | — |
| Purified water | —$^b$ | —$^b$ | —$^b$ | USP | — |
| Capsule Shell, Size 0 Licaps ™ White Opaque | N/A | 1 each | 1 each | None | Capsule shell |
| Total | 100.00 | 200.0 | 400.0 | | |

$^a$Composition is 1:1 w/w ethanol:water solution.
$^b$Removed during the capsule sealing process.

Container/vessel: 12 kg stainless steel
Weigh the following in order:
0.012 kg butylated hydroxytoluene (0.10%)
0.035 kg butylated hydroxyanisole (0.35%)
1.2 kg Compound (1) free base (10%).
0.6 kg Polysorbate 80 (5%) weighed
10.153 kg oleic Acid (equivalent to 84.55 g (84.55%))

Compound (1) capsules, 20 mg or 40 mg, are manufactured through a series of unit process steps. Compound (1) drug substance, oleic acid, polysorbate 80, butylated hydroxytoluene (BHT), and butylated hydroxyanisole (BHA) are mixed until a solution is achieved. The solution is filled into 2-piece hard gelatin capsules. Closed capsules are subsequently sealed with a hydroalcoholic solution, which is evaporated during the sealing process. A vacuum leak test is performed on sealed capsules prior to packaging.

Alternative Formulations

The compound of formula (1) optionally is formulated into a solubilized form with the following agents:
Fatty acids (short, medium, and long chained as well as saturated and unsaturated), typically C4 to C22. Typical fatty acids are lauric acid, capric acid or oleic acid.
Alcohols such as ethanol, benzyl alcohol, glycerol, polyethylene glycol 200, polyethylene glycol 300, polyethylene glycol 400.
Surfactants, including both ionic and non-ionic surfactants. Examples of non-ionic surfactants are fatty acid esters of polyoxyethylene sorbitan, sorbitan fatty acid ester, polyoxyethylene castor oil derivatives, polyoxyethleneglycerol oxystearate, polyethyleneglycol 60, hydrogenated castor oil, and/or block copolymers of ethylene oxide and propylene oxide.
Antioxidants, for example butylated hydroxyanisole (BHA), butylated hydroxytoluene (BHT), vitamin E, and/or vitamin E PEG 1000 succinate for chemical stability.
Viscosity inducer (silicon dioxide, polyethylene glycols, titanium oxide and the like).
And mixtures of the above Encapsulation can be performed in a soft elastic gelatin or a hard gelatin or a hard hydroxypropyl methyl cellulose capsule. The liquid formulation (solution or encapsulated solution) provides improved oral bioavailability.

Capsule Filling

The composition and preparation of the soft elastic gelatin capsule is well known in the art. The composition typically comprises from 30-50% by weight gelatin, 10-40% plasticizer or a blend of plasticizers and about 25-40% by weight water. Plasticizers can be glycerin, sorbitol or sorbitol derivatives, propylene glycol and the like or a combination thereof.

Various methods can be used for manufacturing and filling the soft elastic gelatin capsules such as rotary, liner or accogel machine and the like. Hard gelatin or HPMC capsules can be purchased from. Capsugel, Greenwood, S.C. and other suppliers. Capsules are filled manually or by capsule filling machine.

Formulation Preparation

In general, the compositions of this invention can be prepared in the following manner. The ingredients are mixed in an appropriate vessel size using an overhead mixer (The mixing tank may be purged with nitrogen). The pharmaceutically acceptable fatty acid and the pharmaceutically acceptable antioxidant are mixed at room temperature. (The solution may be warmed to appropriate temperature if needed, for example to about 45 degrees C. in the case of lauric acid, in order to liquefy the fatty acid). The compound of formula (1)

is added and stirred until dissolved. The pharmaceutically acceptable surfactant is added with mixing. The appropriate weight of the resulting mixture is filled into hard gelatin capsules Additional Formulation Compositions

| | |
|---|---|
| Formula (1) compound | 8.0 |
| PEG 400 | 82.8 |
| EtOH | 9.2 |
| Total | 100.0 |
| Formula (1) compound | 8.0 |
| EtOH | 11.0 |
| PG | 7.4 |
| Maisine 35-1 | 36.8 |
| Cremophor RH40 | 36.8 |
| Total | 100.0 |
| Formula (1) compound | 8.0 |
| Oleic Acid | 92.0 |
| Total | 100.0 |
| Formula (1) compound | 8.0 |
| Oleic Acid | 73.6 |
| EtOH | 9.2 |
| Tween 20 | 9.2 |
| Total | 100.0 |
| Formula (1) compound | 8.00% |
| Oleic Acid | 87.40% |
| Tween 80 | 4.60% |
| Total | 100.00% |
| FORMULA (1) COMPOUND | 20.00% |
| Oleic Acid | 80.0% |
| Total | 100.0% |
| FORMULA (1) COMPOUND | 20.00% |
| Oleic Acid | 76.00% |
| Tween 80 | 4.00% |
| Total | 100.00% |
| FORMULA (1) COMPOUND | 8.00 |
| Oleic Acid | 86.47% |
| Tween 80 | 4.60% |
| Aerosil 200 | 0.92% |
| BHT | 0.01% |
| Total | 100.0% |
| FORMULA (1) COMPOUND | 8.00 |
| Oleic Acid | 85.55% |
| Tween 80 | 4.60% |
| Aerosil 200 | 1.84% |
| BHT | 0.01% |
| Total | 100.0% |
| FORMULA (1) COMPOUND | 8.00 |
| Oleic Acid | 85.55% |
| Tween 80 | 4.60% |
| Aerosil 200 | 1.84% |
| BHT | 0.01% |
| Total | 100.0% |
| FORMULA (1) COMPOUND | 10.00 |
| Oleic Acid | 84.55% |
| Tween 80 | 5.00% |
| BHA | 0.35% |
| BHT | 0.1% |
| Total | 100.0% |

EXAMPLE 2a

Micronized Formulation of Compound (1)

Micronized drug substance (Jet mill-00 at 60-80 psi; 3-4 microns average size, about 7-8 sq. meters/g) was dry blended with lactose, microcrystalline cellulose, croscarmellose sodium, sodium lauryl sulfate, tartaric acid, and hydroxypropyl cellulose. The blend was granulated by spraying the blend solution. The granules were dried in a fluid-bed. The dried granules were sized by passing through a mill, and then blended with additional microcrystalline cellulose and croscarmellose sodium. The powder blend was lubricated by adding magnesium stearate and then compressed into tablets using a rotary tablet press. The tablets were subsequently film-coated.

The table below is a summary of various formulations tested in dogs dosed at 40 mg compound (1), corresponding to approximately 4 mg/kg. The table illustrates the superior performance of the solubilized compound (1) formulations.

In-vivo Data Summary

| Dosage Form | Process | Formula | Drug Load (%) | Cmax (μM) | $AUC_{24}$ (μM hr) | F (%) | RSD (%) |
|---|---|---|---|---|---|---|---|
| Solid | Powder Fill[a] | PIC | 50 | 0.7 | 2.9 | 8 | 52 |
| Solubilized | Liquid Fill | Capric acid | 20 | 4.8 | 25 | 79 | 17 |
| | | Lauric acid | 20 | 2.6 | 14.3 | 44 | 29 |
| | | Oleic Acid | 8 | 3.8 | 23 | 67 | 27 |
| | | | 20 | 2.1 | 14 | 44 | 56 |
| | | | 25 | 7.9 | 42 | 125 | 24 |
| Solid | High Shear[a] | SLS only | 20 | 0.4 | 4.4 | 13 | 85 |
| | | SLS & Tartaric | 20 | 0.4 | 2.7 | 8 | 82 |
| | | SLS & Tartaric[b] | 20 | 0.9 | 6.9 | 20 | 67 |
| | Fluid bed[a] | SLS & Tartaric | 20 | 0.3 | 4.4 | 14 | 77 |

[a]Utilizes micronized API
[b]Dosed in dogs treated with pentagastrin to reduce stomach pH

EXAMPLE 3

Antiviral Activity of Compound (1)

The compound of this invention exhibits anti-HCV replicon activity (assay described in WO 05/063744) against both genotypes 1a and 1b, extremely low cytotoxicity (>50,000 nM in Huh-7, HepG2 and MT4 cells), and a highly favorable selectivity index. The compound is substantially less active against genotype 2a.

Activity of Compound 1 Against HCV Genotype 1b and 1a Replicons

HCV genotype 1b (Con-1/lucneo) and 1a (H77/neo) replicon cells were incubated with serial dilutions of compound (1) 2'C-methyl adenosine (2'CMeA) or IFNα for 3 days in the absence or presence of 40 mg/mL human serum albumin (HSA). After incubation, replicon RNA levels in the treated cells were determined by either a luciferase reporter assay (1b replicon) or a quantitative real-time PCR assay (1a replicon) and the data points were used to calculate $EC_{50}$ (50% effective inhibiting concentration) values for the inhibitors. Compound (1) was shown to inhibit both genotype 1b and genotype 1a replicons with $EC_{50}$ values of 0.6 and 3.6 nM, respectively (Table A). In the presence of human serum albumin, the $EC_{50}$ value of Compound (1) was increased to 11 nM.

TABLE A

Activity of Compound (1) against HCV Genotypes 1a and 1b Replicons

| | $EC_{50}$ [nM][a] | | |
|---|---|---|---|
| Compound | HCV 1b-lucneo | HCV 1b-lucneo 40 mg/mL HSA | HCV-1a |
| 1 | 0.6 ± 0.28 | 11 | 3.6 ± 1.4 |
| 2'CMeA | 175 ± 70 | 250 | 170 |
| IFN-α | 2 IU/mL | n.d. | n.d. | n.d., not determined; HSA, human serum albumin
[a]Mean $EC_{50}$ value and standard error determined from at least 4 independent experiments Activity of Compound (1) Against HCV Genotype 1a Replicon and Virus The antiviral activity of compound (1) against HCV genotype 2a was tested in cells chronically infected with the genotype 2a virus as well as in cells replicating a subgenomic 2a replicon. Huh-7 cells containing chronically replicating HCV genotype 2a (J6/JFH-Rluc) virus or subgenomic replicons were cultured with compound (1) or 2'CMeA for 3 days in the absence of human serum albumin. After cultivation, the amount of luciferase in 2a-virus containing cells and HCV NS3 protease activity in the 2a replicon-containing cells was determined using Promega's luciferase assay and a novel time-resolved fluorescence assay, respectively.

The antiviral activity of compound (1) was significantly reduced in both the HCV-2a chronically infected cell culture model ($EC_{50}$=2.9 µM) and the 2a subgenomic replicon model ($EC_{50}$=21.9 µM) compared to Huh-7 cells replicating an HCV-1b subgenomic replicon ($EC_{50}$=0.0006 µM) (Table 2). Taken together, these results suggest that the reduction in potency for compound (1) against HCV genotype 2a may be due to the genotypic differences between genotype 1 and genotype 2 of HCV.

TABLE B

Activity of Compound (1) against HCV Genotypes 1b and 2a

| | $EC_{50}$ [nM][a] | | |
|---|---|---|---|
| Compound | HCV 1b-lucneo (subgenomic replicon) | HCV 2a (subgenomic replicon) | HCV-2a (reporter virus) |
| 1 | 0.6 ± 0.28 | 21898 ± 18972 | 2900 ± 1250 |
| 2'CMeA | 175 ± 70 | 1610 ± 1099 | 194 ± 26 |
| IFN-α | 2 IU/mL | n.d. | 1.2 IU/mL | n.d., not determined; HSA, human serum albumin
[a]Mean $EC_{50}$ value and standard error determined from at least 4 independent experiments Compound (1) was evaluated for its cytotoxicity in a variety of cell types including HCV replicon-containing cell lines (Huh-7, SL3 and MH4) and non-replicon-containing cell lines (HepG2, MT4), using a CellTiter-Glo Luminescence Cell Viability assay (Promega). No toxic effects were observed in any of the cell lines at the highest concentration tested (50 µM) (Table C). These results, coupled with its potent antiviral activity ($EC_{50}$=0.62-3.6 nM) in HCV-1b and HCV-1a replicons, indicates a high selectivity index ($CC_{50}$/$EC_{50}$>13,000-80,000) for compound (1).

TABLE C

Cytotoxicity of compound (1) in HCV Replicon Containing Cell Lines

| | $CC_{50}$ [µM][a] | | | | |
|---|---|---|---|---|---|
| Compound | Huh-7 lucneo[b] | SL3[b] | MH4[b] | HepG2 | MT4 |
| 1 | >50 | >50 | >50 | >50 | >50 |
| 2'CMeA | 7.2 ± 6 | 3.9 | 16 | 24.3 ± 2.1 | 3.5 ± 1.9 | n.d., not determined;
HSA, human serum albumin
[a]Mean $CC_{50}$ value and standard error determined from at least 4 independent experiments
[b]HCV replicon-containing cell lines Anti-HCV Activity of Compound (1) in Combination with IFN In Vitro Pegylated interteron-α (PEG-IFN-α), in combination with ribavirin, represents the current standard of care for HCV-infected patients. In vitro combination studies of compound (1) and IFN-α were performed in replicon cells. Data was analyzed using the MacSynergy template developed by Prichard and Shipman. Results from these studies suggest an additive interaction between compound (1) and IFN-α.

EXAMPLE 4

Antiviral, Pharmacokinetic and Safety Data for Compound (1) in a Phase-1, First-In-Human Trial in HCV Genotype 1-Infected Subjects A randomized, double-blind, placebo controlled trial was designed to evaluate the safety/tolerability, phamacokinetics and antiviral activity of single (in Part A) and multiple (in Part B) doses of Compound (1) (oleic acid solution, above) in subjects chronically infected with HCV genotype 1 (GT-1) without decompensated cirrhosis. Prospective subjects are 18-60 years of age, are HCV treatment naïve, and are in general good health.

In completed Part A, five successive cohorts of 6 subjects were randomized (5:1) to receive single ascending doses of Compound 1 (40, 120, 240, 240-with food, or 480 mg) or placebo. In ongoing Part B, four successive cohorts of 12 subjects are randomized (10:2) to receive multiple ascending doses of Compound 1 (40 mg BID, 120 mg BID, 240 mg QD, 240 mg BID) or placebo, over 8 days.

Thirty-one subjects enrolled in Part A were of mean age 43.6 years, predominantly male (20/31), Caucasian (25/31), and infected with either HCV Genotype-1a (24) or 1b (6). Median (range) baseline HCV viral load was 6.6 $Log^{10}$ RNA IU/mL (5.2-7.3). Single doses of compound (1) were well tolerated, with no serious or treatment-limiting adverse events (AEs) reported. The most common AE was headache. All AEs were mild in severity, with the exception of one moderate headache. There were no Grade 3 or 4 treatment emergent laboratory abnormalities.

Median compound (1) plasma half-life ranged from 10 to 15 hours across cohorts. Systemic exposure was increased approximately 2-fold when compound (1) was administered with a high fat meal. Mean compound (1) concentration 24 hours after the 240 mg fasted dose dosing was ~7-fold higher than the protein binding adjusted in vitro HCV GT-1b Replicon $EC_{50}$ value. Following single-dose exposure, maximal antiviral effect was observed at 24 hours, with median declines ranging from 0.46 to 1.49 $Log^{10}$ HCV RNA IU/mL across cohorts. Individual HCV RNA declines among all compound (1) recipients ranged from 0.19 to 2.54 $log^{10}$ IU/mL following single-dose exposure.

This is the first clinical demonstration of antiviral activity of compound (1). Single dose exposure to compound (1) was well tolerated, demonstrated favorable PK properties and potent antiviral activity.

EXAMPLE 5

The anti-HCV replicon activity of compound (1) was compared to that of a prior art (WO 05/063744) compound, the compound of formula (4)

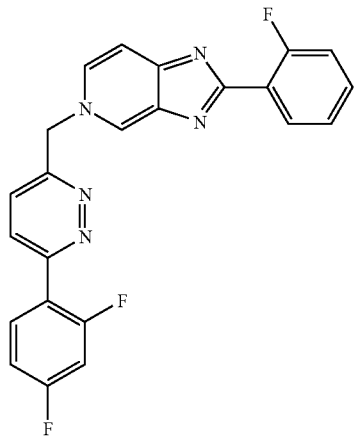
(4)

Unexpectedly compound (1) was about 330 times more potent than the compound of formula (4).

We claim:

1. A method for the preparation of compound (1) comprising providing the intermediate (2)

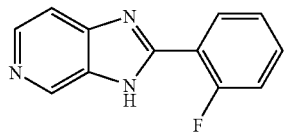
(2)

coupling 2,4-bis(trifluoromethyl)phenylboronic acid to 3-chloro-6-methylpyridazine to produce compound (2a)

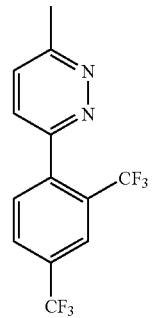
(2a)

treating compound (2a) with a chlorinating agent to produce the alkylating agent (3)

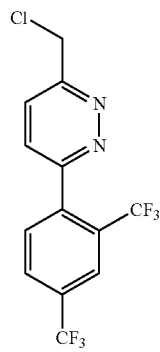
(3)

and using alkylating agent (3) to alkylate intermediate (2) under basic conditions to yield compound (1)

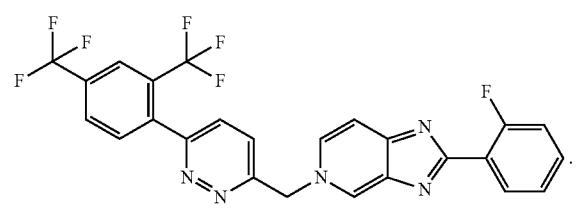
(1)

* * * * *